United States Patent
Hehli et al.

(10) Patent No.: US 7,862,596 B2
(45) Date of Patent: Jan. 4, 2011

(54) PLASTIC IMPLANT FOR OSTEOSYNTHESIS

(75) Inventors: Markus Hehli, Frauenkirch (CH); Reto Frei, Platz (CH); Georg Duda, Berlin (DE)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 10/314,406

(22) Filed: Dec. 9, 2002

(65) Prior Publication Data

US 2003/0149433 A1 Aug. 7, 2003

Related U.S. Application Data

(63) Continuation of application No. PCT/CH00/00315, filed on Jun. 9, 2000.

(51) Int. Cl.
*A61B 17/80* (2006.01)
(52) U.S. Cl. .................................. 606/286
(58) Field of Classification Search ......... 606/69–71, 606/96, 76, 77, 232, 67, 62, 65; 602/47
See application file for complete search history.

(56) References Cited

U.S. PATENT DOCUMENTS

| | | | | |
|---|---|---|---|---|
| 4,037,980 A | * | 7/1977 | Haentjens | 403/336 |
| 4,355,429 A | * | 10/1982 | Mittelmeier et al. | 623/20.14 |
| 4,863,475 A | * | 9/1989 | Andersen et al. | 128/898 |
| 4,905,680 A | * | 3/1990 | Tunc | 606/280 |
| 5,009,665 A | * | 4/1991 | Serbousek et al. | 623/22.39 |
| 5,201,737 A | * | 4/1993 | Leibinger et al. | 606/284 |
| 5,290,281 A | * | 3/1994 | Tschakaloff | 606/28 |
| 5,370,702 A | * | 12/1994 | Jones | 623/22.34 |
| 5,380,328 A | | 1/1995 | Morgan | |
| 5,476,467 A | | 12/1995 | Benoist | |
| 5,549,612 A | * | 8/1996 | Yapp et al. | 606/69 |
| 5,723,008 A | * | 3/1998 | Gordon | 606/75 |

(Continued)

FOREIGN PATENT DOCUMENTS

DE 299 13 390 U1 * 9/1999

(Continued)

OTHER PUBLICATIONS

English Translation of DE 29913390 U1.*

(Continued)

*Primary Examiner*—Anu Ramana
(74) *Attorney, Agent, or Firm*—Morgan Lewis & Bockius LLP

(57) ABSTRACT

The invention relates to an osteosynthesis implant (1) that preferably consists of a bioresorbable plastic material. The inventive implant receives the longitudinal fixation elements (10) to be anchored in the bone, especially in the form of wires, nails, pins or screws. The openings destined to receive the fixation elements (10) do not completely extend through the implant (1) like in conventional bone plates or intramedullary nails but are degenerated to indents (2) in the surface of the implant (1) so that they may serve as a guide for the fixation elements (10) to be guided through the implant (1). The inventive implant (1) allows insertion of the fixation elements (10) in the bone diverging angles and crossing one another, so that the fixation elements (10) extending intramedullarly or in the spongiosa are primarily prevented from migrating in a proximal or distal direction.

14 Claims, 2 Drawing Sheets

U.S. PATENT DOCUMENTS

| | | | |
|---|---|---|---|
| 5,728,099 A * | 3/1998 | Tellman et al. | 606/65 |
| 5,925,077 A * | 7/1999 | Williamson et al. | 623/22.34 |
| 5,931,839 A * | 8/1999 | Medoff | 606/69 |
| 6,030,162 A * | 2/2000 | Huebner | 411/413 |
| 6,123,709 A * | 9/2000 | Jones | 606/281 |
| 6,206,881 B1 * | 3/2001 | Frigg et al. | 606/69 |
| 6,221,075 B1 * | 4/2001 | Tormala et al. | 606/77 |
| 6,344,042 B1 | 2/2002 | Curtis et al. | |
| 6,383,190 B1 | 5/2002 | Preissman | |
| 6,517,542 B1 * | 2/2003 | Papay et al. | 606/73 |
| 2003/0135281 A1 * | 7/2003 | Hanssen | 623/22.35 |

FOREIGN PATENT DOCUMENTS

| | | |
|---|---|---|
| EP | 0 574 091 A2 | 12/1993 |
| JP | 03-085179 | 4/1991 |
| JP | 04-221538 | 8/1992 |
| JP | 07-313586 | 12/1995 |
| JP | 08-024347 | 1/1996 |
| JP | 09-201330 | 8/1997 |
| WO | WO 99/38447 * | 8/1999 |
| WO | WO-01/32100 A2 | 5/2001 |

OTHER PUBLICATIONS

"European Patent Application No. 04750971.6, Communication mailed Jun. 12, 2008", 5 pgs.

"International Patent Application Serial No. PCT/CH00/000315 (1806/PCT), International Preliminary Examination Report dated Feb. 26, 2002" (w/ English Translation), 4 pgs.

"Japanese Application No. 2002-506661, Notice of the Reason for the Rejection mailed Feb. 27, 2008", (w/ English Translation),7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999),1079-1091).

Stile, R. A., et al., "Synthesis and Characterization of Injectable Poly(N-isopropylacrylannide)-Based Hydrogels That Support Tissue Formation in Vitro", *Macromolecules*, 32, (1999),7370-7379.

* cited by examiner

PLASTIC IMPLANT FOR OSTEOSYNTHESIS

CROSS REFERENCE TO RELATED APPLICATION

This is a continuation of International Application No. PCT/CH00/00315, filed Jun. 9, 2000.

FIELD OF THE INVENTION

The invention relates to a bone fixation system for osteosynthesis that includes an implant and longitudinal fixation elements, which may be in the form of wires, nails, pins, or screws, that are received by the implant for anchoring in bone.

The implant can be formed as a bone plate or an intramedullary nail. In its plate-like embodiment it can act as an internal fixation means for osteosynthesis, for example, to the proximal humerus or other areas near the joint of tubular bones.

BACKGROUND OF THE INVENTION

From U.S. Pat. No. 5,476,467 to Benoist, a guiding template that has shafts in the manner of a fan is known for guiding Kirschner wires. The disadvantages of this arrangement consist of the fact that the fixation elements (Kirschner wires) can only be guided parallel to one another through the guiding template. Due to the shaft structure of the template, it does not lie directly on the bone so that the length of the wires to be introduced is unnecessarily extended.

SUMMARY OF THE INVENTION

Here the invention aims to provide a remedy. The objective of the invention is to provide an osteosynthetic implant which has no penetrating holes to receive longitudinal fixation elements to be anchored in the bone, but rather only a number of indentations in its surface that serve as an aid to positioning and guiding to introduce the fixation elements, at diverging angles and crossing one another, first through the implant and then into bone.

The implant permits the introduction of Fixation elements, at diverging angles and crossing one another, into the bone so that primarily a migration of the fixation elements running intramedullarily or in the spongiosa is preventing proximally as well as distally.

The invention realizes the objective with an implant that has surface indentations that do not penetrate completely through the implant, but rather serve as an aid to positioning and guiding the fixation elements there through as well as with a fixation device that includes this implant and at least one fixation element for fastening the implant in or on a bone.

The indentations, preferably formed conically or cylindrically, in the upper side of the implant serve as centering elements for the penetrating holes of the guiding plate, for example, with Kirschner wires. The Kirschner wires have, on their front part, a drill bit whose length corresponds preferably to at least the thickness of the plate-like implant or to the diameter of the implant in the form of an intramedullary nail. Furthermore, the Kirschner wires have an outer thread that serves to secure against axial displacement in the implant so that a migration of the Kirschner wires in the implant is prevented. The Kirschner wires can be drilled into the implant at angles to its surface that can be freely chosen by the surgeon, preferably in directions skewed relative to one another in order to achieve an optimal fracture fixation. The position and angle of the Kirschner wires can thus be chosen according to the fracture to be cared for.

Thus the advantage can be achieved that a minimally invasive operation technology can be applied, with implant material to be inserted minimally. The implant according to the invention is suitable in particular, due to the possibility of arranging the fixation elements in three dimensions, to osteosynthesis of bones that are osteoporotic or weakened by disease. The stability of the osteosynthesis is thus produced primarily by the bolts/wires and their crosswise positioning in the bone. Due to the fact that the implant lies directly on the bone, the free length of the wires to be introduced is reduced to a minimum. Thereby an early load of the fracture site is possible, and thus an earlier utilization of the affected connective masses and, in the ideal case, quicker healing.

A preferred extension consists of the case wherein the implant consists of a bioresorbing or biodegradable plastic that is preferably chosen from the group of polylactates. The indentations are expediently disposed in a regular grid on the upper side of the implant.

In a development as a bone plate or as plate-like guiding bodies, the implant preferably has an approximately circular upper side with indentations disposed in concentric circles. The number of indentations is between 3 and 100, preferably between 7 and 40. Typically 10 indentations are provided. Expediently the indentations expand conically toward the upper side. The conical indentations advantageously have a conical angle ranging from 30° to 120°, preferably from 40° to 100°. The indentations have on the upper side a diameter ranging from 1.0 to 3.0 mm, preferably between 1.5 to 2.2 mm (typically 2 mm). The depth of the indentations is in the 0.6 to 1.5 mm range, preferably between 0.8 to 1.2 mm (typically 1 mm).

In the preferred embodiment as plate-like implant, its upper side is preferably formed convexly in order to achieve a better conformity to the surface of the bone. Its thickness is in the 2 to 6 mm range, preferably between 2.5 to 4.0 mm. The upper side expediently has a surface area ranging from 3 to 15cm$^2$, preferably between 4 to 10 cm$^2$ (typically 4.5 cm$^2$).

In a preferred form of embodiment, the fixation element used as implant has a drill bit with a length from 4 to 10 mm, preferably from 5 to 8 mm. The drill bit should preferably correspond at least to the thickness of the implant.

The fixation element is expediently provided with an outer thread, preferably over a length from 30 to 80 mm. It preferably has no head at its back end and has a uniform diameter, seen over its entire length, preferably in the 1 to 6 mm range (typically in the 2 to 5 mm range).

BRIEF DESCRIPTION OF THE DRAWINGS

The invention and extensions of the invention are explained in more detail in the following with the aid of the partially schematic representations of an embodiment example. Shown are.

DETAILED DESCRIPTION OF THE INVENTION

Figure 1:
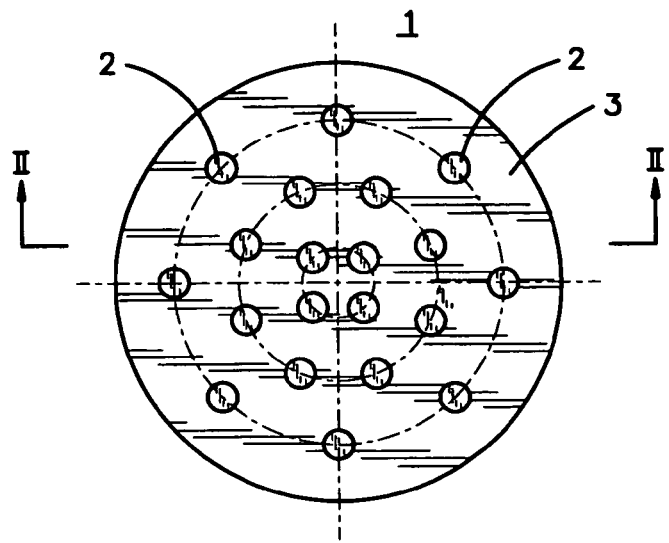
FIG. 1 a top view of a plate-like implant formed as a guiding body.
Figure 1A:
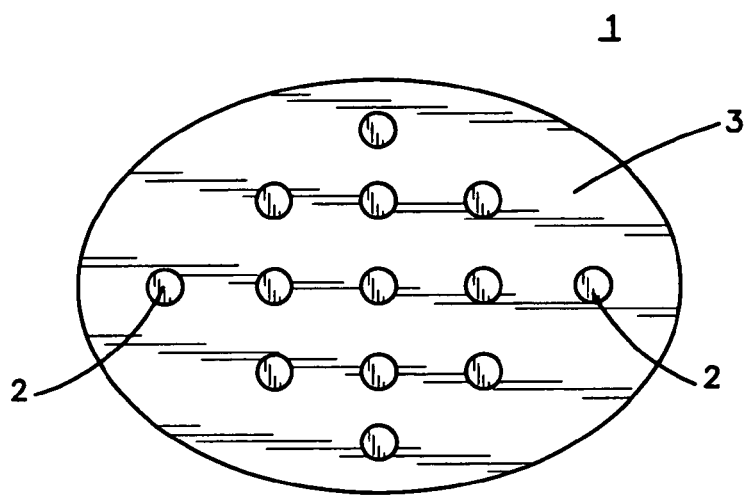
FIG. 1A a top view of an alternate plate-like implant.
Figure 2:
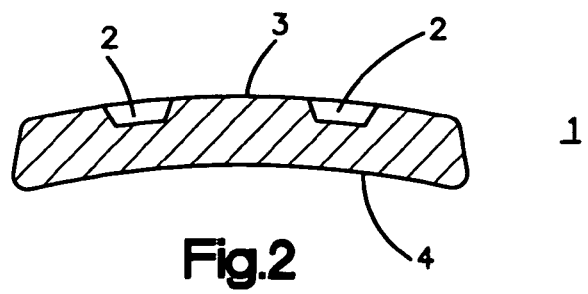
FIG. 2 a cross-section through the implant along the line II-II in FIG. 1 in the area of two indentations.

The implant 1 represented in FIGS. 1 and 2 consists of a 3-mm-thick, arched plate of a biodegradable plastic, in particular a polylactate, suitable for implantation in the human body. The implant 1 has a convex upper side 3 and a concave lower side 4 intended for contact with the bone. In the upper side 3, a plurality of indentations 2 in the form of funnels expanding conically toward the upper side 3 are introduced. The lower side 4 of the implant 1 is preferably made to conform to the bone surface to be applied in order to achieve as good and broad a bone contact surface as possible.

Figure 3:
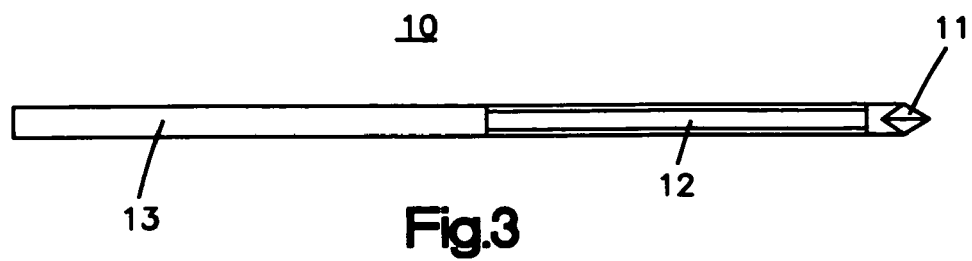
FIG. 3 a view of a fixation element in the form of a Kirschner wire.

Represented in FIG. 3, the fixation element 10 in the form of a customary Kirschner wire has no head at its back end 13 so that it has a uniform diameter over its entire length. At its front end the fixation element 10 has a drill bit 11 as well as an outer thread 12.

Figure 4:
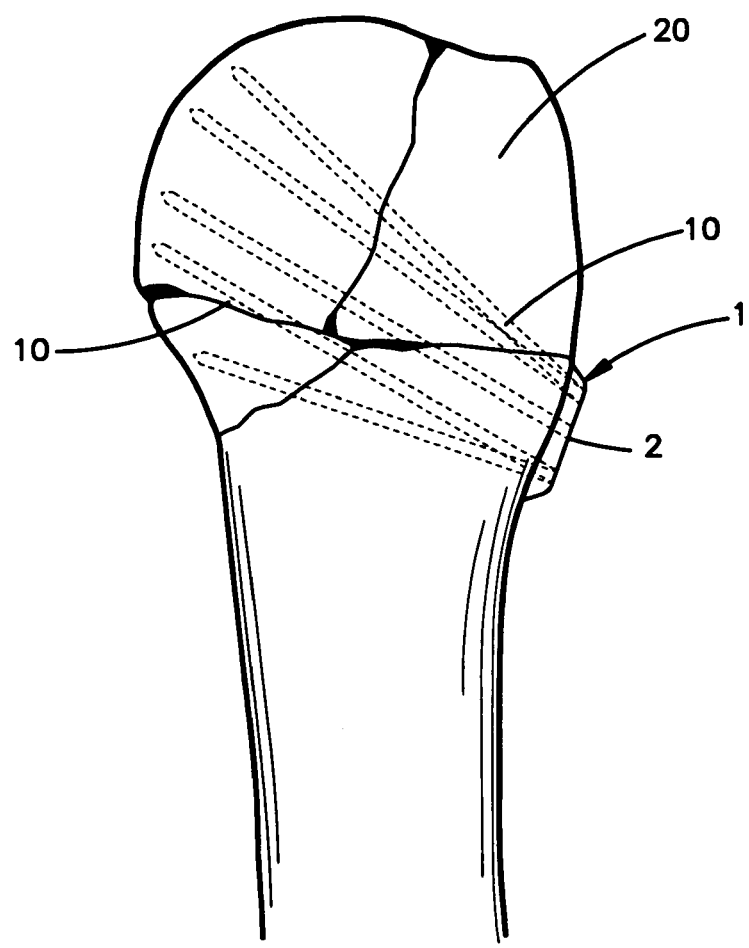
FIG. 4 a view of a fractured humerus with an implant that is fastened to the bone with a plurality of Kirschner wires drilled therein.

The implant 1 can be introduced through a minimal incision in the body, for example, in the area of the proximal humerus 20 (FIG. 4) to which it can be fastened with the fixation means 10. In so doing, the additional use of bone cement is not ruled out. Since the plate-like implant 1 has sufficient indentations 2, they can serve to fasten bands to bone fragments of the humerus 20. In so doing, the three-dimensional, skewed arrangement of the fixation means 10 prevents their loosening so that on the whole a greatly improved stability of fixation results.

The invention claimed is:

1. A bone fixation system comprising:
at least two headless fixation elements for anchoring in bone; and
a bioresorbable plate having an upper surface, a lower surface, and a thickness between about 2 mm and about 6 mm; and a plurality of indentations formed on the upper surface for locating a starting point while also permitting a range of starting angles for any one of the headless fixation elements; the indentations having a diameter at the upper surface, and a full plate thickness surrounding the diameter at the upper surface, and being conically shaped with a conical angle between 30 degrees and 120 degrees; wherein:
each headless fixation element is sized to be received within any one of the indentations and configured to penetrate through a remaining portion of the plate defined by a bottom surface of the indentation and the lower surface of the plate, each headless fixation element including an outer thread on a front portion thereof;
each headless fixation element having an outer surface configured to contact an inner surface of the indentation after penetration of the headless fixation element through the plate;
the bottom surfaces of two or more indentations each have an area of sufficient size to allow the headless fixation elements to be drilled into the plate at angles to the lower surface in directions skewed relative to one another;
such that the two headless fixation elements are positioned crosswise into a bone after penetration of the two headless fixation elements through the plate and into the bone; and
the plate is completely devoid of any holes which initially penetrate completely through the plate.

2. The system according to claim 1, wherein the plate includes a plurality of indentations disposed in a grid on the upper surface.

3. The system according to claim 1, wherein the plate has an oval shape.

4. The system according to claim 1, wherein the upper surface of the plate is convex and the lower surface is concave.

5. The system according to claim 1, wherein the plate includes between 3 and 100 indentations.

6. The system according to claim 1, wherein the plate is made from a polylactates.

7. The system according to claim 1, wherein the outer thread has a length within a range of 30 and 80 mm.

8. The bone fixation system of claim 1, wherein each headless fixation element has a uniform diameter over substantially its entire length.

9. The bone fixation system of claim 1, wherein each headless fixation element has a self-drilling tip on one end.

10. The bone fixation system of claim 1, wherein the length of the self drilling tip substantially corresponds to the thickness of the plate.

11. The bone fixation system of claim 1, further comprising a plurality of indentations disposed on the upper surface and the plate has a circular configuration with the indentations disposed in concentric circles.

12. A bone fixation system comprising:
at least two headless fixation elements for anchoring in bone; and
a bioresorbable plate having an upper surface, a lower surface, and a thickness in a range of about 2 mm and about 6 mm; and a plurality of indentations defined by the upper surface for guiding and receiving any one of the headless fixation elements; the indentations having a diameter at the upper surface, and a full plate thickness surrounding the diameter at the upper surface, and being conically shaped with a conical angle between 30 degrees and 120 degrees; wherein:
each headless fixation element is sized to be received within any one of the indentations and configured to penetrate through a remaining portion of the plate defined by a bottom surface of the indentation and the lower surface of the plate, each headless fixation element including an outer thread;
each headless fixation element having an outer surface configured to contact an inner surface of the indentation after penetration of the headless fixation element through the plate;
the bottom surfaces of two or more indentations each have an area effective for allowing the headless fixation elements to be drilled into the plate at angles to the lower surface in directions skewed relative to one another;
such that two headless fixation elements are positioned crosswise into a bone after penetration of two headless fixation elements through the plate and into the bone; and
the plate is free of any holes which initially penetrate through the plate.

13. The bone fixation system of claim 12, wherein the plate has a circular configuration and a plurality of indentations disposed in concentric circles on the upper surface of the plate.

14. A bone fixation system comprising:
a bioresorbable plate having an upper surface, a lower surface, and a thickness between about 2 mm and about 6 mm; and a plurality of indentations formed on the upper surface; the indentations having a diameter at the upper surface of, and a full plate thickness surrounding the diameter at the upper surface, and being conically shaped with a conical angle between 30 degrees and 120 degrees;

a plurality of headless fixation elements penetrating through a remaining portion of the plate defined by a bottom surface of the indentation and the lower surface of the plate at a drilled angle with respect to the lower surface, each headless fixation element including an outer thread on a front portion thereof;

each headless fixation element having an outer surface configured to contact an inner surface of the indentation after penetration of the headless fixation element through the plate;

wherein the headless fixation elements are positioned crosswise with respect to each other, and wherein at least one indentation remains without a headless fixation element penetrating a bottom surface.

* * * * *